United States Patent [19]

LeClerc et al.

[11] Patent Number: 5,364,502
[45] Date of Patent: Nov. 15, 1994

[54] CONTROL OF RECOVERY BOILER OPERATION BY IR SPECTROSCOPY

[75] Inventors: Denys F. LeClerc, Surrey; Robert M. Hogikyan, Burnaby, both of Canada

[73] Assignee: Pulp & Paper Research Institute of Canada, Quebec, Canada

[21] Appl. No.: 124,055

[22] Filed: Sep. 17, 1993

Related U.S. Application Data

[62] Division of Ser. No. 910,379, Jul. 8, 1992, Pat. No. 5,282,931.

[51] Int. Cl.$^5$ .................. D21C 7/12; D21C 11/12
[52] U.S. Cl. ................... 162/49; 162/30.1; 162/31; 162/252
[58] Field of Search .......... 162/49, 30.1, 31, 252, 162/62, 198, 238, 263

[56] References Cited

U.S. PATENT DOCUMENTS

| | | | |
|---|---|---|---|
| 3,553,075 | 1/1971 | Rivers | 162/49 |
| 3,607,083 | 9/9171 | Chowdhry | 23/230 R |
| 4,540,468 | 9/1985 | Genco et al. | 162/49 |
| 4,743,339 | 5/1988 | Faix et al. | 162/49 |
| 5,082,526 | 1/1992 | Dorris | 162/30.11 |

FOREIGN PATENT DOCUMENTS

| | | |
|---|---|---|
| 944905 | 4/1974 | Canada . |
| 1230171 | 12/1987 | Canada . |

OTHER PUBLICATIONS

Vroom, "The H Factor" 1957 Pulp and Paper Magazine of Canada, pp. 228–231, Convention Issue.
Ingruber et al., "The Effect of Hydrogen Ion . . . ", TAPPI, Dec. 1967 vol. 50, No. 12, pp. 597–614.
Hatton, "Development of Yield Protection . . . ", TAPPI, Jul. 1973 vol. 56, No. 7, pp. 97–100.
Wilson, "An Automatic Analyzer for Control of . . . " Svensk Papperstidning. ARG 75, No. 13, Jul. 15, 1972, pp. 522–523.
Maiorov et al., "Study of Continuous Absorption in Infrared . . . ", 1976 Zh. Fiz. Khim. 50 (11) pp. 2817–2820.
Sjöström, "The Behavoir of Wood Polysaccharides . . . ", TAPPI, Sep. 1977 vol. 60, No. 9, pp. 151–154.
Ross et al., "Behavior of 4–O–Methylglucuronoxylan . . . ", TAPPI, vol. 48 No. 6, Jun. 1965, pp. 376–380.
Analysis of Sulphate Process Black Liquors, Standard J. 15P, Oct. 1991.
Grace, "Black Liquor Evaporation", Pulp & Paper Manufacture, 1983 Third Edition, TAPPI, pp. 477–479.
Kappa Number of Pulp, TAPPI Standard T636CM-85, 1984.
Analysis of Soda and Sulfate Black Liquor, TAPPI Standard T625cm-85, 1984.
Hatton, "The Significance of Residual Effective . . . ", TAPPI Proceedings 1984 Pulping Conference, pp. 469–478.

(List continued on next page.)

*Primary Examiner*—W. Gary Jones
*Assistant Examiner*—Dean T. Nguyen
*Attorney, Agent, or Firm*—Millen, White, Zelano & Branigan

[57] ABSTRACT

A direct monitoring and control method is provided for on-line measurement of effective alkali, carbonate, sulfate and thiosulfate concentrations in process liquors for the production of kraft pulp. The control method eliminates frequent sampling, and the need for frequent equipment maintenance. The method includes the steps of withdrawing samples of a liquor from the kraft manufacturing process, subjecting the samples to infrared spectrophotometry at predetermined wave numbers to produce peak-absorbance measurements relative to a background spectrum of water, determining peak absorbance for different alkali concentrations, correlating relationships between the peak-absorbance measurements of samples with the peak absorbance for different alkali concentrations to determine optimum effective alkali in the samples, and controlling at least one process parameter to obtain effective alkali of the liquor.

7 Claims, 10 Drawing Sheets

OTHER PUBLICATIONS

Rydholm, "Pulping Processes", Robert E. Krieger Pub. Co., 1985, p. 604.
Hough, "Chemical Recovery in the Alkaline Pulping Processes" TAPPI Press 1985, p. 107.
Williamson, "New Robot Analyzer Offers Optimum . . . ", Pulp & Paper Canada 87:2 (1986), p. 13.
Faix et al., "Continuous Process Control of Pulping . . . ", TAPPI Proceeding 1989 Wood & Pulping Chemistry, pp. 1–8.
Dorris et al., "Conductivity Sensors For Slaker Control . . . Part I" J. of Pulp & Paper Science, vol. 15, No. 4, Jul. 1989, pp. J122–131.
Michell, "Kappa Number Determination in Kraft Pulping . . . ", TAPPI Journal Apr. 1990, pp. 235–236.
Dorris, "Conductivity Sensors for Slaker control . . . Part II", Pulp & Paper Canada 92:2 (1990) pp. 45–51.
Watson et al., "On–Line Analysis of Caustic Streams by . . . ", Spectroscopy vol. 2, No. 1, 1990, pp. 44–48.
Melling et al., "Remote FTIR Spectroscopy . . . ", American Laboratory Dec. 1991, pp. 32c–32g.
Milanova et al., "On the Determination of Residual . . . ", TAPPI Press 1991 Pulping Conference, pp. 289–297.

CONTROL OF RECOVERY BOILER OPERATION BY IR SPECTROSCOPY

This application is a divisional of U.S. Ser. No. 07/910,379 filed on Jul. 8, 1992 and issued as U.S. Pat. No. 5,282,931.

TECHNICAL FIELD

The present invention relates to kraft pulp manufacturing processes and more specifically to a rapid method for determining and controlling effective alkali and inorganic salt concentrations during the digesting, recausticizing and recovery operations of a kraft mill.

BACKGROUND ART

Kraft pulping is performed by cooking wood chips in a highly alkaline liquor which selectively dissolves lignin and releases the cellulosic fibers from the wooden matrix. The two major chemicals in the liquor are sodium hydroxide and sodium sulfide. Sodium sulfide, also a strong alkali, readily hydrolyses in water producing sodium hydroxide. The sulfidity is the amount of sodium sulfide in solution divided by the total amount of sodium sulfide and sodium hydroxide. The sulfidity is usually expressed as a percentage which varies between 20 and 30% in pulping liquors. The total amount of sodium hydroxide in solution is called effective alkali (EA) before pulping or residual effective alkali (REA) after pulping. Timely knowledge of the REA ensures good control of the pulping process.

At the beginning of the kraft process white liquor is fed to the digester. This liquor contains a high amount of effective alkali. At the exit of the digester the spent liquor or black liquor is extracted from the digester. This black liquor contains low levels of effective alkali. Black liquor also contains large amounts of organic compounds which are burned in a recovery furnace. The mass of inorganic residues, called smelt, is then dissolved to form green liquor having a low concentration of effective alkali and a high concentration of sodium carbonate. White liquor is then regenerated from the green liquor by causticizing the carbonate through the addition of lime. After the recausticizing operation, a small residual amount of sodium carbonate is carried over to the digester. The total amount of sodium hydroxide, sodium sulfide and sodium carbonate is called the total titratable alkali. The causticizing efficiency (CE) is usually defined as the difference in the amounts of sodium hydroxide between the white and green liquors divided by the amount of sodium carbonate in the green liquor. Sodium sulfate and sodium thiosulfate, together with sodium carbonate, represent a dead load in the liquor recycling system. Sodium thiosulfate is particularly undesirable in processed liquors because of the potential for corrosion of metal surfaces in contact with these liquors. The reduction efficiency (RE) is defined as the amount of green liquor sodium sulfide, divided by the combined amounts of sodium sulfide and sodium sulfate in either green liquor or the smelt. A reduction in dead load chemicals has a beneficial impact on kraft mill operations, thus there is a need for better control of all aspects of kraft mill operations and more efficient use of all chemicals involved in the process. The timely knowledge of the white liquor charge of effective alkali and black liquor charge of residual effective alkali would close the control loop in the digester and minimize alkali and lime consumption.

Various methods of measuring effective alkali have been proposed, however most of these measurements have to be corrected for temperature effects and interferences by other cations and anions, as well as organics. Conductivity sensors have been implemented in some mills, and these give indirect measurement of effective alkali. They may be suitable for on-line measurements of effective alkali in white or green liquors, however they are not suitable for black liquor due to a high solids content and the presence of salts from weak organic acids in the black liquor. On-line measurements of effective alkali in black liquors have been attempted in a number of ways ranging from on-line calorimeters to on-line automatic conductimetric titration methods. None of those systems is straightforward. Titration methods encounter maintenance problems, thus most mill site measurements still rely on laboratory standard methods involving precipitating carbonate and phenoxide ions with barium chloride before performing the titration.

The control of continuous digesters is performed by keeping the chip and white liquor feeds at preset levels which are determined by the overall production rate. Control is performed by adjusting the temperature profile of the cook through the H-factor and determining the resultant blow line kappa number. Kappa number is a measure of pulp lignin content. One disadvantage of this method is that it assumes uniform chip moisture content and digester temperature. Since the pulp must be analyzed in the laboratory for lignin content, there is always a delay in controlling the process.

Other methods to analyze organic content have been developed to correlate the amount of organics with pulp yield and kappa number. On-line methods however have not been entirely satisfactory. In U.S. Pat. No. 4,743,339 Faix et al proposes a method for determining effective alkali in black liquor based upon on-line infrared circular attenuated reflectance measurements. Faix et al also report [TAPPI proceedings, 1989 Wood and Pulping Chemistry Symposium, Raleigh, N.C.] that one is able to measure the consumption of sodium sulfite and the appearance of lignosulfonates during alkaline sulfite anthraquinone methanol pulping, but the results were not very accurate because of spectral non-linearities due to the precipitation of dissolved compounds. Certain limitations were therefore found with this method.

Michell in TAPPI Journal 73(4) 235, 1990, suggested a similar method for kappa number determination by correlating the increase in the integrated band intensity at a wave number of 1118 $cm^{-1}$ with decreasing kappa number. Unfortunately, this region is also prone to interferences from the primary and secondary hydroxyl groups in carbohydrates. No attempts were made by either Michell or Faix et al to evaluate the spectral region situated between wave numbers of 1800 to 2900 $cm^{-1}$ for useful information.

To be useful the direct measurement of effective alkali in process liquors must be free of interferences from both inorganic and organic compounds. Up to now, no infrared spectrophotometric method for directly measuring effective alkali in pulping liquors has been developed and implemented for routine use in pulp and paper manufacturing.

DISCLOSURE OF INVENTION

The present invention provides a direct monitoring and control method for the on-line measurement of effective alkali, residual effective alkali, carbonate, sulfate and thiosulfate concentrations in process liquors for the production of kraft pulp. The control method is on-line and largely eliminates the need for frequent equipment maintenance, sample pretreatment and the use of chemical reagents. High sample throughput allows many process streams to be multiplexed to a single analyzer.

Samples of process liquors are analyzed by infrared spectrophotometry, the baseline corrected absorbance of the liquor is measured at a predetermined wavelength, the chemical composition of the liquor is then calculated, the absorbance is correlated with the concentration of the absorbing compound and this correlation is made by comparing results previously obtained with standard samples. Process samples are also analyzed by standard analytical methods to establish a correlation with the data obtained by infrared spectrophotometry.

The on-line analytical procedure for residual effective alkali is used to analyze digester liquor samples from either batch or continuous digesters. The on-line analytical sensor can also be used to determine sulfate, thiosulfate, carbonate and hydroxide levels in green and white liquors. The reduction efficiency in the recovery boiler and the causticizing efficiency may also be calculated. Thus, the sensor of the present invention replaces automatic titrators and conductivity sensors and gives much needed information on the carbonate, thiosulfate and sulfate levels in process liquors while improving the control of scaling in the multi-effect evaporators. Furthermore, the sensor measures the extent of white and black liquor oxidation by monitoring thiosulfate levels as well as performing semi-quantitative determination of the extent of cellulose degradation.

In one embodiment the present invention provides a method for determining and controlling effective alkali of liquors in a kraft pulp manufacturing process, comprising the steps of: withdrawing samples of a liquor from the process, subjecting the samples to infrared spectrophotometry at predetermined wave numbers to produce peak-absorbance measurements relative to a background spectrum of water, determining peak absorbance for different alkali concentrations, correlating relationships between the peak-absorbance measurements of samples with the peak absorbance for different alkali concentrations to determine optimum effective alkali in the samples, and controlling at least one process parameter to obtain optimum effective alkali of the liquor.

BRIEF DESCRIPTION OF DRAWINGS

In drawings which illustrate embodiments of the present invention.

MODES FOR CARRYING OUT THE INVENTION

Figure 1:
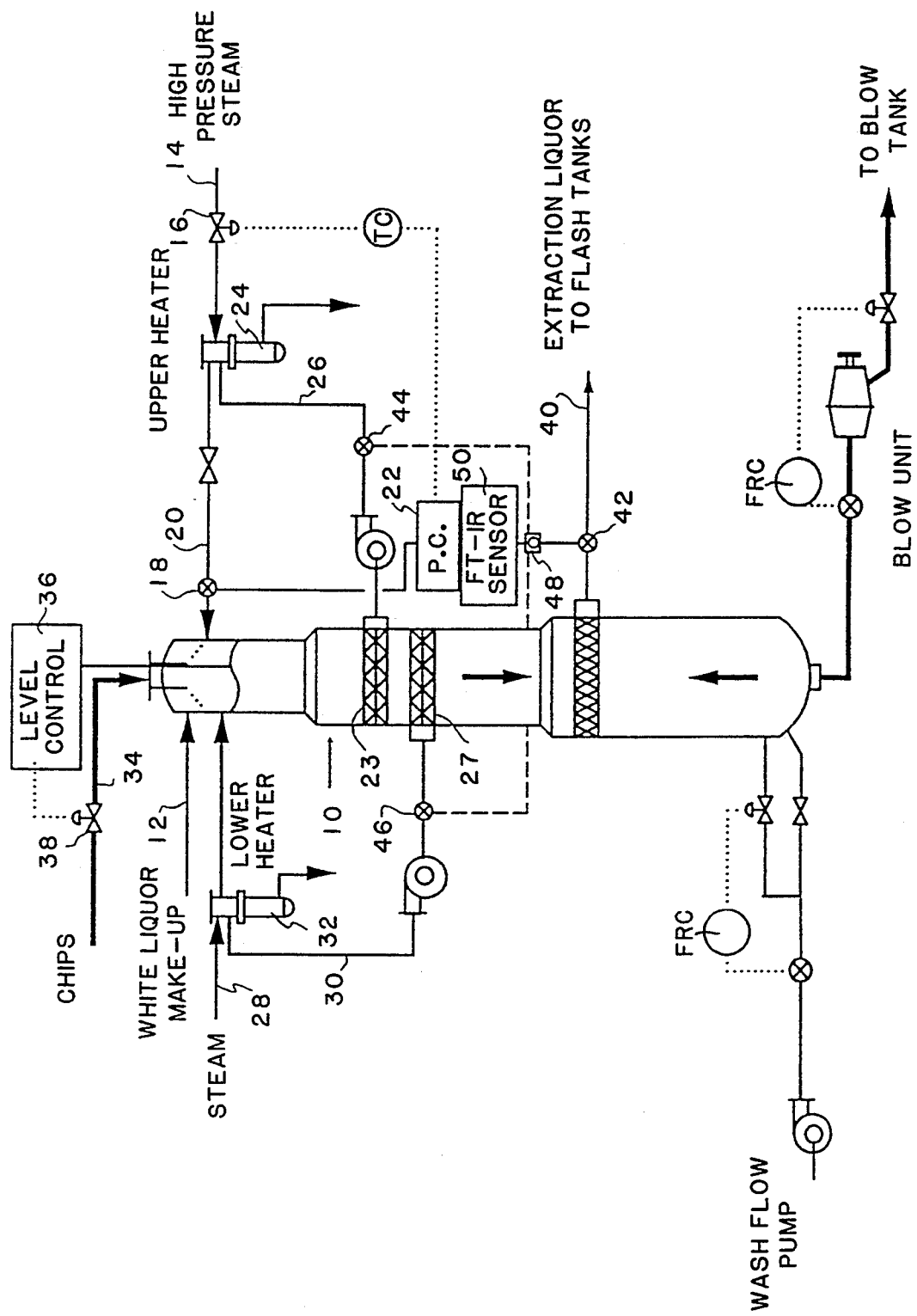
FIG. 1 is a diagrammatic view of a pulp digester complete with sensing and control apparatus according to one embodiment of the present invention.

FIG. 1 shows a diagrammatic representation of a continuous type Kamyr digester and of a control system as embodied by the invention. This control system may be used to monitor the EA consumption during the impregnation stage of a modified continuous cooking pulping operation. Referring to FIG. 1, a digester 10 is shown with makeup white liquor supplied through line 12. The liquor in the digester 10 is indirectly heated through a transfer line by high pressure steam supplied through a steam supply line 14 and valve 16. Temperature readings of the cooking liquor are taken by a heat sensor 18 located in steam line 20 and communicated to a computer 22. Black liquor is withdrawn from the digester 10 through the upper extraction screen 23 and then sent through an upper heater 24 using a recirculating loop 26. A second steam line 28 provides steam to a second recirculating loop 30 in which the liquor is withdrawn from digester 10 through the lower extraction screen 27 and sent to a lower heater 32.

Chips are fed to the digester 10 through line 34. A chip level control 36 controls the level in the digester by means of valve 38. Samples from the digester are continuously withdrawn from the extraction liquor line 40 at withdrawal point 42. For other tests, samples are withdrawn from the sample point 44 in the upper heater loop 26 or sample point 46 in the lower heater loop 30.

The samples are fed through a flow cell 48 for continuous measurement of the infrared circular attenuated total reflectance (CATR) of the liquor. Alternatively, a square section attenuated total reflectance cell may be used instead. The CATR cell 48 admits infrared light that is detected by a Fourier transform infrared (FT-IR) spectrometer 50. The spectrometer 50 correlates the liquor infrared absorbance at a wave number of about 1882 cm$^{-1}$ with the residual effective alkali of the flowing liquor. The signal from the spectrometer 50 is fed to the computer 22 to control either the cooking duration through the H-factor, which is done by regulating the flow of steam through valve 16 in line 14, or the flow of white liquor through line 12. The extraction liquor flows through line 40 to the flash tanks (not shown) on its way to the recovery cycle.

A batch digester is controlled similarly to the continuous digester shown in FIG. 1. Samples are drawn at different digestion times. Modifications may be made by regulating the flow of black liquor recirculation or adjusting the temperature and the cooking time. Alternatively, the infrared light from the spectrometer may be transmitted by infrared fiber optics. These fibers communicate between an instrumentation cubicle and a nearby flow cell through which liquor flows from remote locations.

Figure 2:
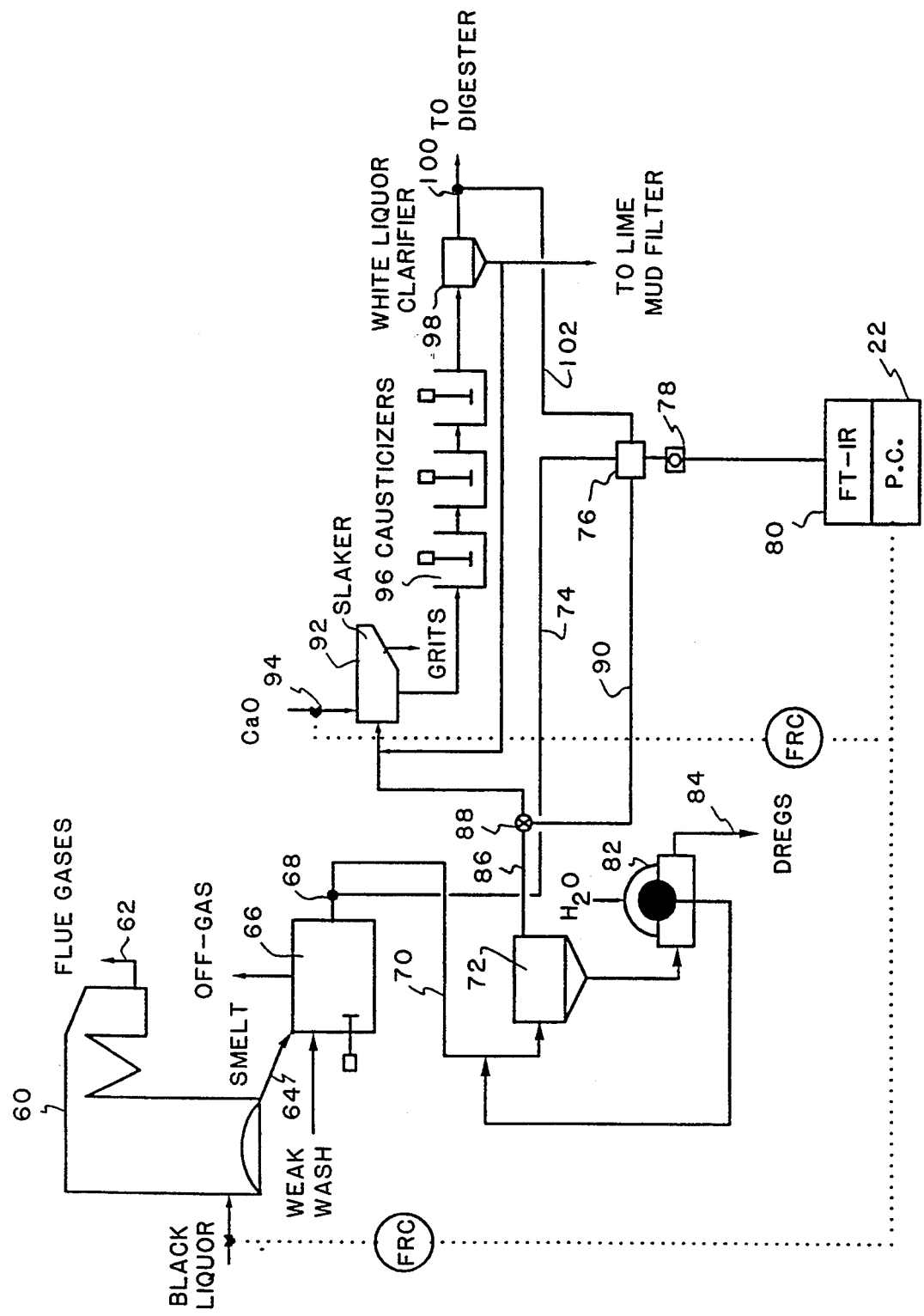
FIG. 2 is a diagrammatic view of the recovery and recausticizing systems, complete with sensing and control apparatus according to another embodiment of the present invention.

FIG. 2 shows a diagrammatic view of the recovery and of the recausticizing systems, complete with a sensing and control apparatus embodied by the invention. Black liquor passes through multi-effect evaporators (not shown) and is admitted to the recovery furnace 60 to generate flue gases 62 and smelt 64. The smelt 64 flows to the smelt dissolving tank 66 to form green liquor. Green liquor samples are taken at sample withdrawal point 68 in line 70 leading to the green liquor clarifier 72. The samples are fed through a small bore conduit 74 into a sample stream multiplexer 76 and a flow through CATR cell 78 which admits infrared light that is detected by a Fourier transform spectrometer 80. The spectrometer 80 correlates the infrared absorbance of the liquor at wave numbers of about 1104 cm$^{-1}$ and 1001 cm$^{-1}$ with the sulfate and thiosulfate concentrations of the liquor, respectively. Readings from the spectrometer 80 on both concentrations are then transferred to computer 22 which indirectly calculates an arbitrary value for the reduction efficiency by setting a minimum target value for sulfate concentration. The quantity of thiosulfate and sulfate coming into the tank with the weak wash liquor is relatively minor and does not interfere with this measurement.

The computer is then adapted to adjust operational variables of the recovery furnace to improve the reduction of sulfate and thiosulfate to sulfide in the lower furnace. Alternatively, this information may be passed to an operator for manual adjustments. The liquor then proceeds to the green liquor clarifier 72. Dreg deposits are filtered in the dregs filter 82 before passing through the disposal line 84. Green liquor recovered from the dregs filter 82 flows from the clarifier 72 through line 86 and is sampled at sample withdrawal point 88. The sampled liquor passes through line 90 to the sample stream multiplexer 76. It is then analyzed with flow through cell 78 and spectrometer 80. The spectrometer correlates the respective carbonate and hydroxide concentrations with their corresponding infrared absorbances at wave numbers of about 1386 cm$^{-1}$ and 1882 cm$^{-1}$.

Liquor in line 86 from the clarifier 72 enters the slaker 92 where a variable quantity of calcium oxide is added through valve 94 to form calcium hydroxide. A series of three or more causticizers 96 allow most of the sodium carbonate to react with the calcium hydroxide to form sodium hydroxide and calcium carbonate. The resulting suspension then proceeds to the white liquor clarifier 98. The clarified liquor is then sampled at withdrawal point 100 at the exit of the white liquor clarifier 98. The white liquor is sampled through line 102 to the multiplexer 76 and the flow through cell 78 where it is analyzed for carbonate and hydroxide by spectrometer 80. The sampling of the different sample withdrawal points 68, 88 and 100 occurs in sequence through the multiplexer 76. Lime mud from the clarifier 98 is then withdrawn and calcined in a lime kiln (not shown) to form quicklime (CaO). This is then recycled to the slaker 92.

The output data about the liquor collected from sample withdrawal points 88 and 100 are used to monitor carbonate and hydroxide levels, and to estimate the causticizing efficiency (CE) given a suitable time delay corresponding to the duration of the causticizing reaction by computer 22. The computer 22 also controls valve 94 to adjust the lime feed rate to the slaker 92.

A combined system of pipes, light guides or infrared fiber optic cables are used for remote sensing in the recovery and recausticizing systems to sample liquor from multiple locations and thereby minimize system costs by allowing multiple streams to be analyzed by a single FT-IR apparatus.

Experiments were conducted utilizing a Perkin-Elmer [Norwalk, Conn.] 1610 FT-IR spectrometer to record all spectra. Spectra recorded were the results of 64 averaged scans over a spectral range of 4400 cm$^{-1}$ (2.25 micrometers) to 650 cm$^{-1}$ (15.50 micrometers). The spectra were run at room temperature using a micro-boat germanium-crystal version of the CIRCLE CELL (T.M.) CATR accessory supplied by Spectra-Tech [Norwalk, Conn.]. Oxidized strong black liquor (BL), diluted to 23% solids, was used as the source of spent liquor. Three pairs of green (GL) and white (WL) liquor samples, along with the black liquor sample, were analyzed using both FT-IR and selected TAPPI, CPPA and SCAN standard methods for EA, sulfate and carbonate, respectively. Standard solutions of sodium hydroxide, sodium carbonate, sodium sulfate and sodium thiosulfate were prepared (percent w/w) by direct weighing. Solutions of sodium hydroxide were prepared separately (9.5, 8.5, 7.5, 6.5, 5.5, 4.5, 3.5, 2.5, 1.5, 0.5 percent w/w) by direct weighing on a Mettler PJ3000 analytical balance with a readability of 0.01 g. Standard solutions (5, 4, 3, 2, 1, 0.5 and 0.2 percent w/w) were similarly prepared for sodium carbonate, sodium sulfate and sodium thiosulfate. Higher-concentration solution of sodium carbonate (10, 9, 8, 7, 6, and 5 percent w/w) were also prepared to simulate the higher levels found in kraft mill green liquors. Concentrations were converted to g/l (as $Na_2O$) for further data analysis. Standard white liquor solutions (5, 15, 25, 35, 45, 55, 65 g/l as $Na_2O$; sulfidity: 25%) were also prepared. The transmittance spectra of these solutions were then ratioed against pure water spectra, and the results transformed to absorbance values. Peak-height absorbances were read at wave values of about 1001 cm$^{-1}$ for thiosulfate, about 1104 cm$^{-1}$ for sulfate, about 1386 cm$^{-1}$ for carbonate, and about 1882 cm$^{-1}$ for hydroxide. No interferences or infrared peaks due to hydrosulfide or polysulfide ions were found. A Beer's law calibration plot was then established from peak-absorbance measurements using linear regression parameters. These are given in Table I for EA, carbonate, sulfate and thiosulfate. Integrated-absorbance calibration curves were also calculated for carbonate levels typical of green liquors. Curves were drawn on paper and the area between a wave number of about 1200 cm$^{-1}$ was estimated by cutting out the paper surface. This surface was then weighted with an analytical balance. This calculation can also routinely be performed on other commercial systems by integration software. To verify the precision and accuracy of the CATR method, selected results for EA, REA and dead-load levels for actual mill samples were obtained. For these samples, background corrections to the absorbance were performed to account for baseline shifts due to high concentrations of sodium hydroxide and/or organic acids. Mill results (expressed as g/l $Na_2O$) are summarized in Table II, and details are discussed in the following examples.

TABLE I

| REGRESSION PARAMETER | Regression parameters | | | |
| --- | --- | --- | --- | --- |
| | Effective Alkali (as $Na_2O$) | Sodium Carbonate (as $Na_2O$) | Sodium Sulfate (as $Na_2O$) | Sodium Thiosulfate (as $Na_2O$) |
| Constant | 0.0052 | 0.0171 | 0.0007 | 0.0005 |
| Std Err of Y Est | 0.0025 | 0.0040 | 0.0003 | 0.0005 |
| R Squared | 0.9973 | 0.9910 | 0.9993 | 0.9799 |
| No. of Observations | 10 | 10 | 5 | 5 |
| Degrees of Freedom | 8 | 8 | 3 | 3 |
| X Coefficient | 0.0013 | 0.0044 | 0.0066 | 0.0026 |
| Std Err of Coef. | 0.0001 | 0.0002 | 0.0001 | 0.0002 |

TABLE II

| | Mill sample results | | | | | |
| --- | --- | --- | --- | --- | --- | --- |
| | NaOH (g/l, as $Na_2O$) | | $Na_2CO_3$ (g/l, as $Na_2O$) | | $Na_2SO_4$ (g/l, as $Na_2O$) | |
| SAMPLE | FT-IR | ACTUAL[1] | FT-IR | ACTUAL[2] | FT-IR | ACTUAL[3] |
| WL-1 | 82.2 | 83.3 | 22.4 | 21.3 | 3.3 | 3.5 |
| GL-1 | 26.0 | 26.3 | 76.3[5] | 80.0 | 4.2 | 4.2 |
| WL-2 | 80.7 | 81.8 | 18.3 | 17.9 | 7.0 | 6.7 |
| GL-2 | 26.6 | 28.3 | 77.4[5] | 73.3 | 6.4 | 6.2 |
| WL-3 | 81.6 | 84.6 | 23.5 | 22.5 | 2.9 | 3.0 |
| GL-3 | 24.4 | 25.5 | 74.0[5] | 74.3 | 2.4 | 2.8 |
| BL | 6.3 | 6.8 | n/a | n/a | 3.9[6] | 4.3[4,6] |

[1] by CPPA J.12 standard procedure;
[2] by SCAN N-2 standard procedure
[3] by SCAN N-3 standard procedure;
[4] by TAPPI T-624 standard procedure
[5] by integrated absorbances;
[6] wt % on dry black-liquor solids (23.1%)

EXAMPLE 1

Figure 3:
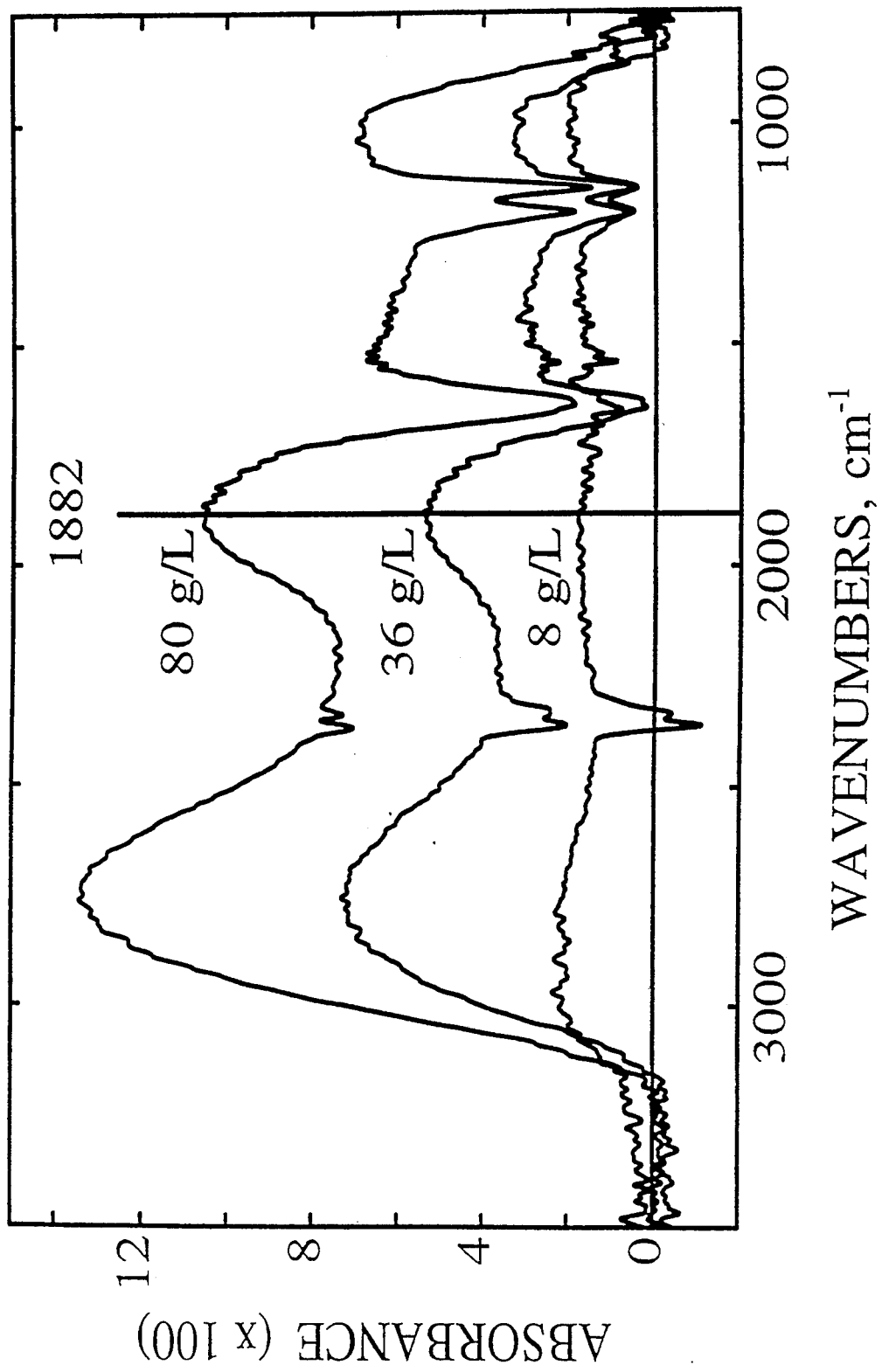
FIG. 3 is a graph of absorbance versus wave numbers showing the change in band absorbance at a wave number of 1882 cm$^{-1}$ for three effective alkali concentrations.
Figure 4:
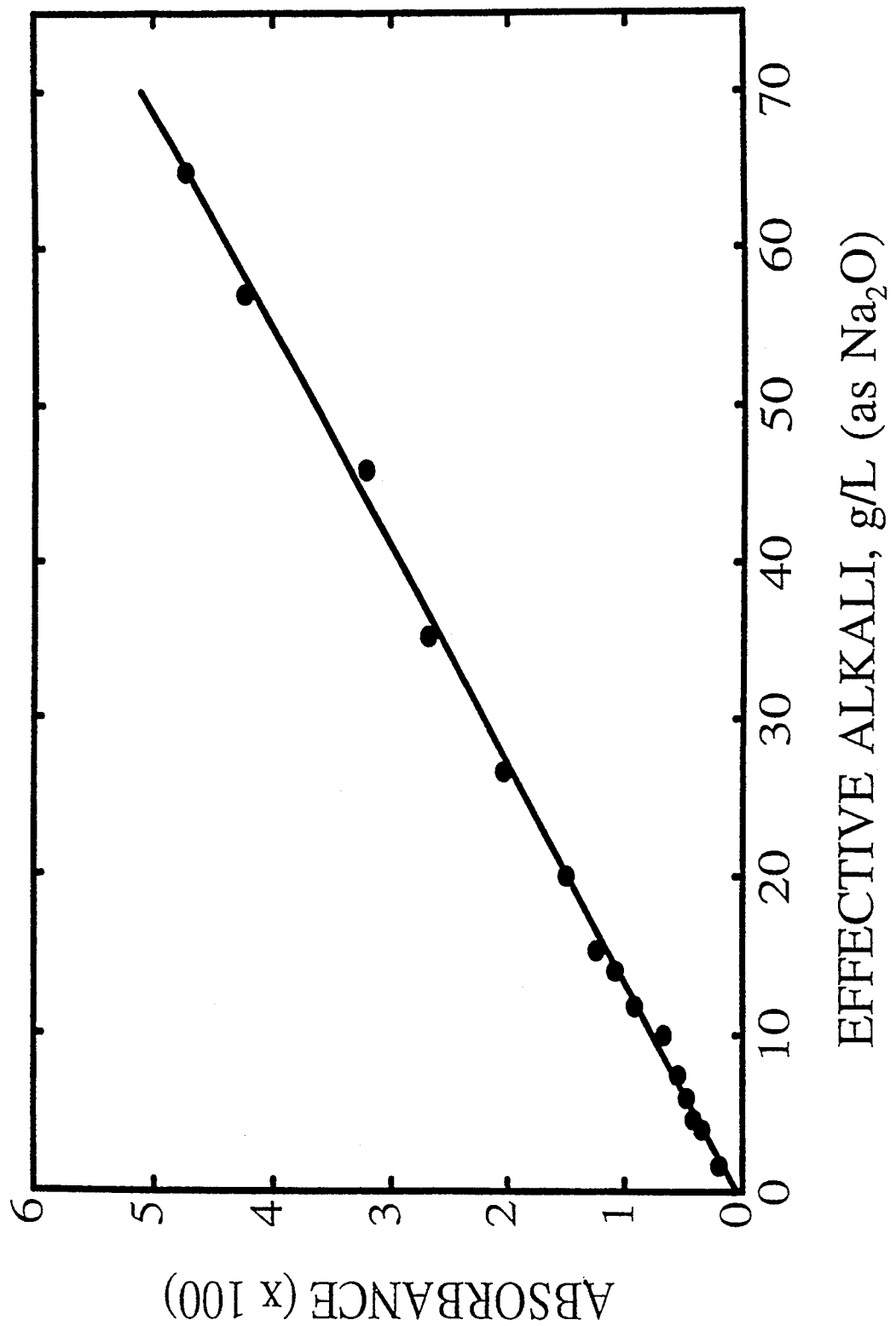
FIG. 4 is a calibration graph of absorbance versus effective alkali concentration for fifteen effective alkali concentrations and a sulfidity of 25%.

The infrared spectrum for three different EA concentrations is seen in FIG. 3. An example of a typical calibration curve is shown in FIG. 4 for white liquor. Careful least-squares regression analysis (least-squares curve fitting) of the data (Table I, Column 1) shows that EA levels are accurately measured by infrared spectrophotometry in kraft liquors. The standard deviation for both the absorbance and the intercept of the calibration curve shown in FIG. 4 is about 0.00015. Since the slope is about 0.00072, this translates into a concentration error of 0.4 g/l (as $Na_2O$) at the $2\sigma$ confidence level. Precision is thus fair, but could be improved by doing more replicate runs or using a more sensitive detector. The observed peak at a wave number of about 1882 $cm^{-1}$ (FIG. 3) is due to sodium hydroxide monohydrate. This hydrate forms when a sufficient amount of sodium hydroxide is dissolved in water. The amount of monohydrate present in the solution is thus directly proportional to the amount of EA. This peak therefore gives an accurate indication of the EA levels in the liquors. High levels of sodium hydroxide also cause small, upward reproducible shifts in the baseline near 1001 $cm^{-1}$, and 1386 $cm^{-1}$ wave numbers. The baseline shifts represent about 10% of the total absorbance. These baseline absorbances can be estimated at a wavelength situated near the base of a peak and must be subtracted from the peak absorbances readings at the respective carbonate, thiosulfate and sulfate peaks to obtain the absorbance due to the compound. The peak situated at a wave number of about 1882 $cm^{-1}$ is easy to detect and does not interfere with any other peaks. The information obtained from this peak can therefore be used to correct for the small, corresponding baseline shift at other wavelengths, using multilinear regression techniques. Sodium hydroxide shows another peak at a wave number of about 2736 $cm^{-1}$. EA results for three white and green liquors (Table II, Column 1) agree with those obtained with standard methods.

EXAMPLE 2

Figure 5:
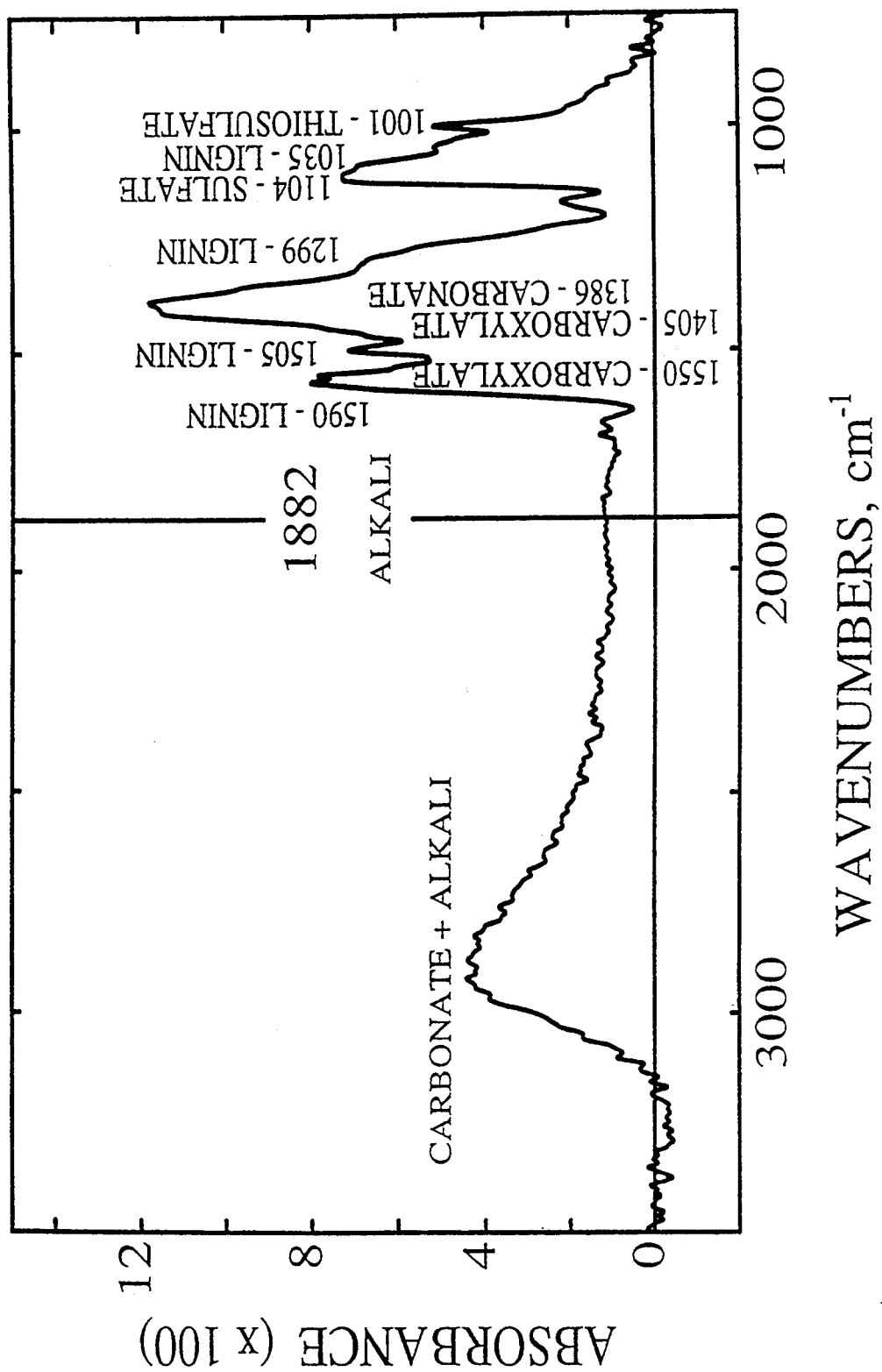
FIG. 5 is a graph of black liquor absorbance versus wave numbers.

A spectrum of digester black liquor is shown in FIG. 5. The sodium hydroxide peak at a wave number of about 1882 $cm^{-1}$ is weak. Nevertheless, this spectral feature is still clearly visible. It was also found that the absorbance at a wave number of about 1030 $cm^{-1}$ could be used as a reliable baseline for the sulfate peak to correct for the combined signal due to lignin and carbohydrate compounds absorbing in this region. The result for sulfate is corrected by subtracting the value of the baseline absorbance at a wave number of about 1030 $cm^{-1}$ from the peak absorbance at a wave number of about 1104 $cm^{-1}$. Even though a sharp peak for lignin can be seen at 1491 $cm^{-1}$, the other peaks due to lignin (1299, 1118 and 1030 $cm^{-1}$) are weak and appear mostly as shoulders. For example, the lignin peak at 1118 $cm^{-1}$ is small and does not interfere with sulfate determination. Although peaks due to hemicellulose (1355 $cm^{-1}$, shoulder), lignin (1299 $cm^{-1}$, shoulder), inorganic carbonate (1386 $cm^{-1}$) and carboxylate ions of organic acids (1403 $cm^{-1}$) strongly overlap, the maximum of the carbonate peak is still clearly visible at a wave number of about 1386 $cm^{-1}$. However, the precise determination of carbonate in black liquor is difficult because of the strong overlap of those peaks. Similarly, the multiple peaks at wave numbers of about 1550 $cm^{-1}$ represent overlapping bands from syringyl lignin (1575 $cm^{-1}$) and carboxylate groups of organic acids (1545 $cm^{-1}$) resulting from hemicellulose degradation. The lack of hydroxyl bands near 3500 $cm^{-1}$ in FIG. 5 also confirms that these groups are present as sodium salts in alkaline solutions. Results for EA and sulfate in black liquor (BL) shown in Table II agree with those obtained from standard methods.

EXAMPLE 3

Figure 6:
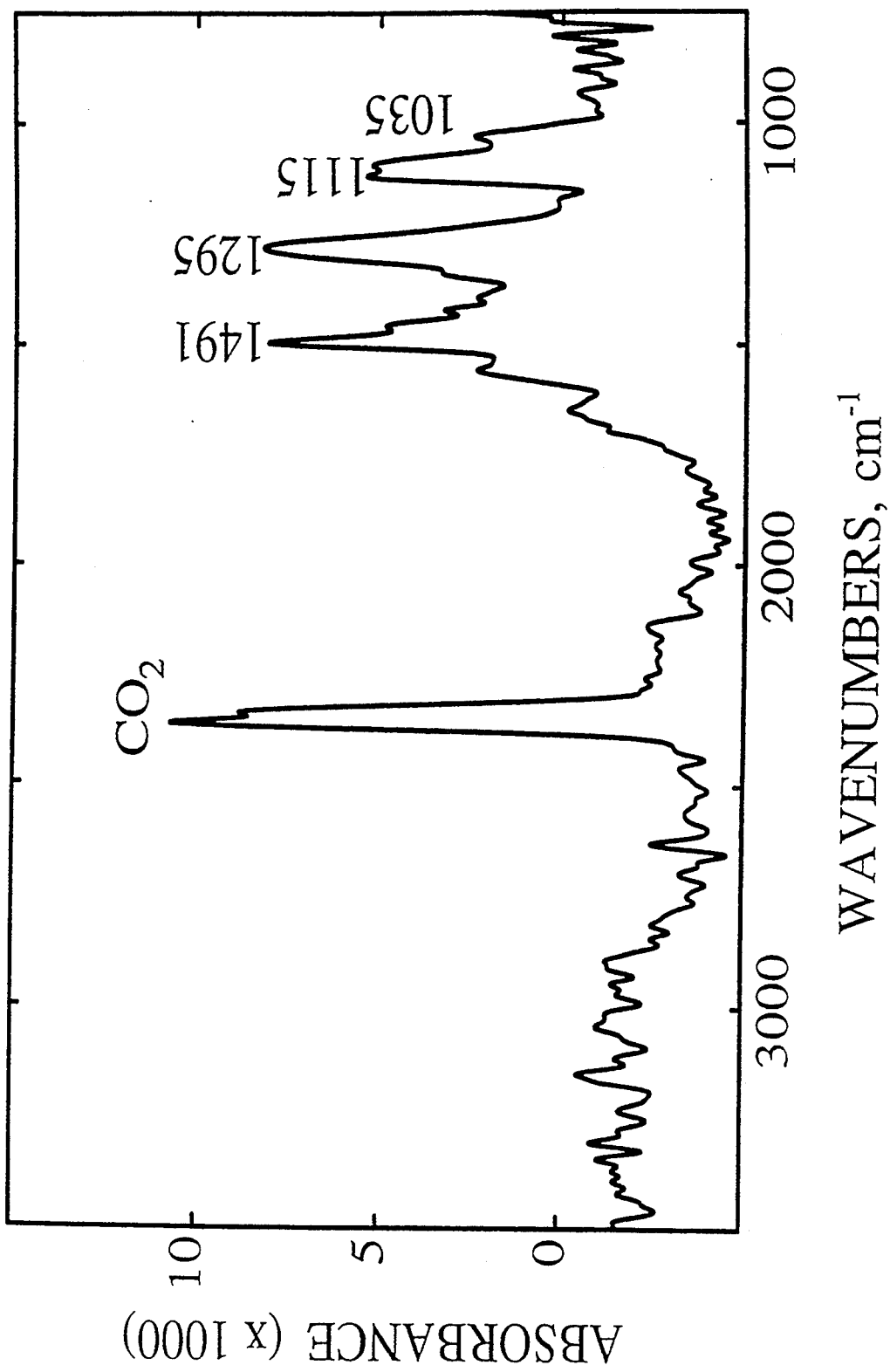
FIG. 6 is a graph of kraft pine lignin absorbance versus wave numbers.
Figure 7:
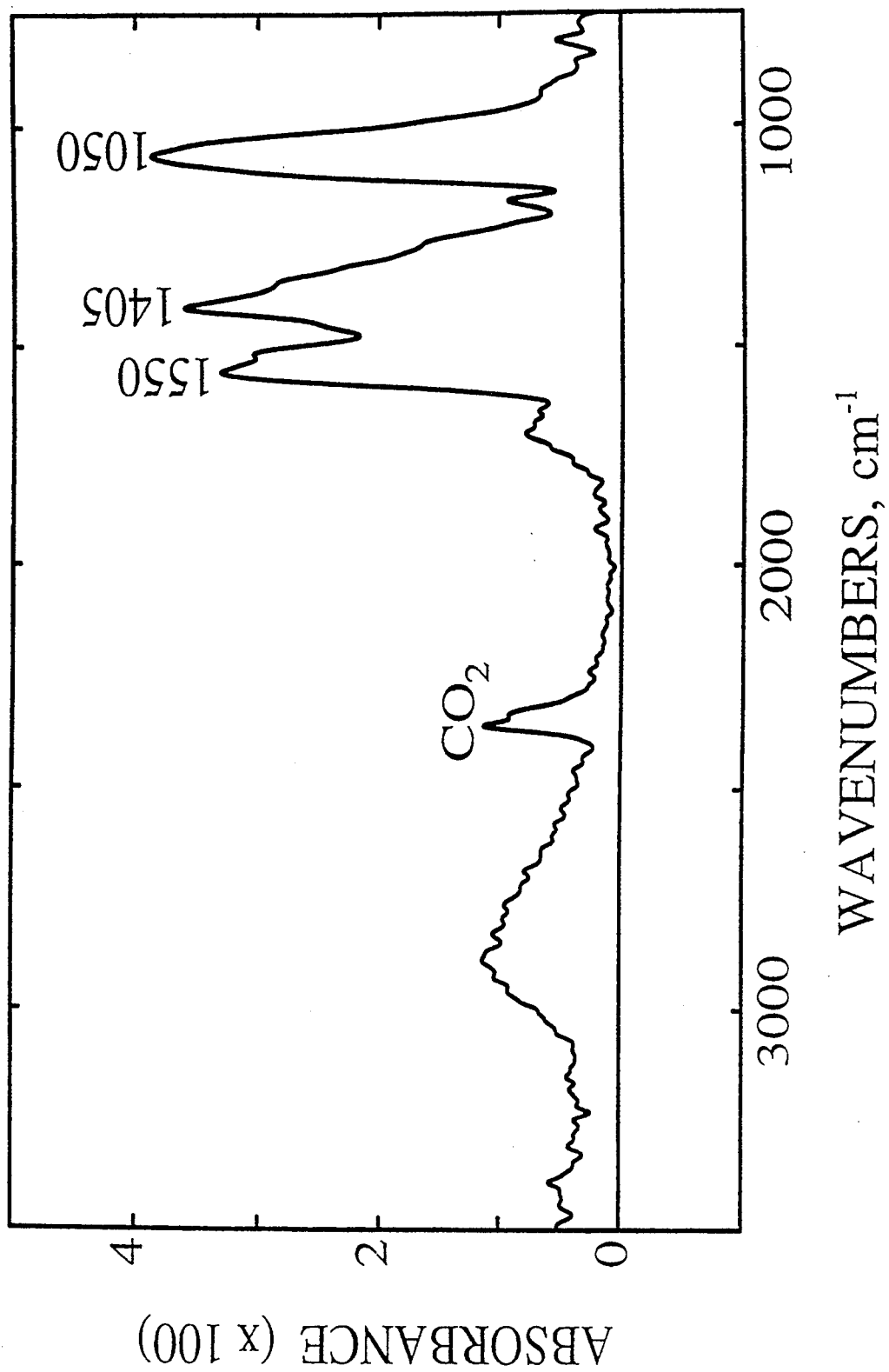
FIG. 7 is a graph of glucoisosaccharinic acid absorbance versus wave numbers.

Peak assignments given in Example 2 for lignin were verified by dissolving 60 grams INDULIN AT [Westvaco, Chemical Division, Charleston Heights, S.C.] kraft pine lignin polymer in one liter of white liquor (EA=35 g/l; sulfidity=25%). The sample spectrum was scanned against a white liquor background. The CATR spectrum of pure lignin is shown in FIG. 6, with four peaks situated at wave numbers of about 1491, 1295, 1115 and 1035 cm$^{-1}$. The match between these peaks and their identification in FIG. 5 is apparent. Similarly, glucose was dissolved in a caustic solution (EA=75 g/l, sulfidity=0%) and heated to form glucoisosaccharinic acid. The sample spectrum was scanned against a caustic background. The CATR spectrum of glucoisosaccharinic acid is shown in FIG. 7, with intense peaks at a wave number of about 1550 and 1400 cm$^{-1}$ due to carboxylate ions and a broad absorption peak extending from about 1025 to about 1075 cm$^{-1}$ due to the carbon-oxygen single bonds of primary and secondary hydroxyl groups. The match with the peaks assigned to carboxylate salts of carbohydrate degradation products in FIG. 5 is also apparent.

EXAMPLE 4

Figure 8:
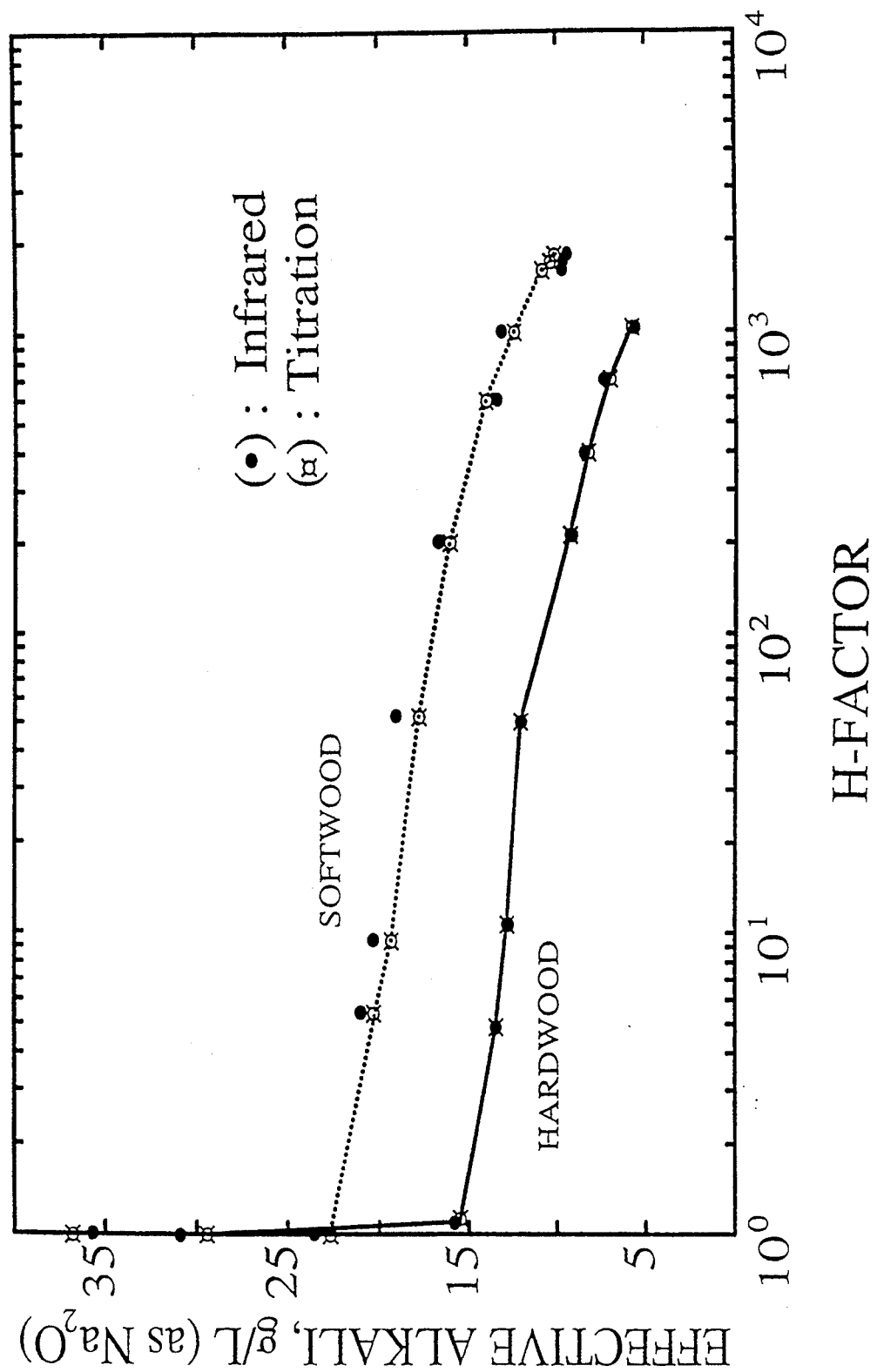
FIG. 8 is a graph of the evolution of effective alkali concentration of black liquor versus the logarithm of the H-factor obtained during cooking of hardwood and softwood chips.
Figure 9:
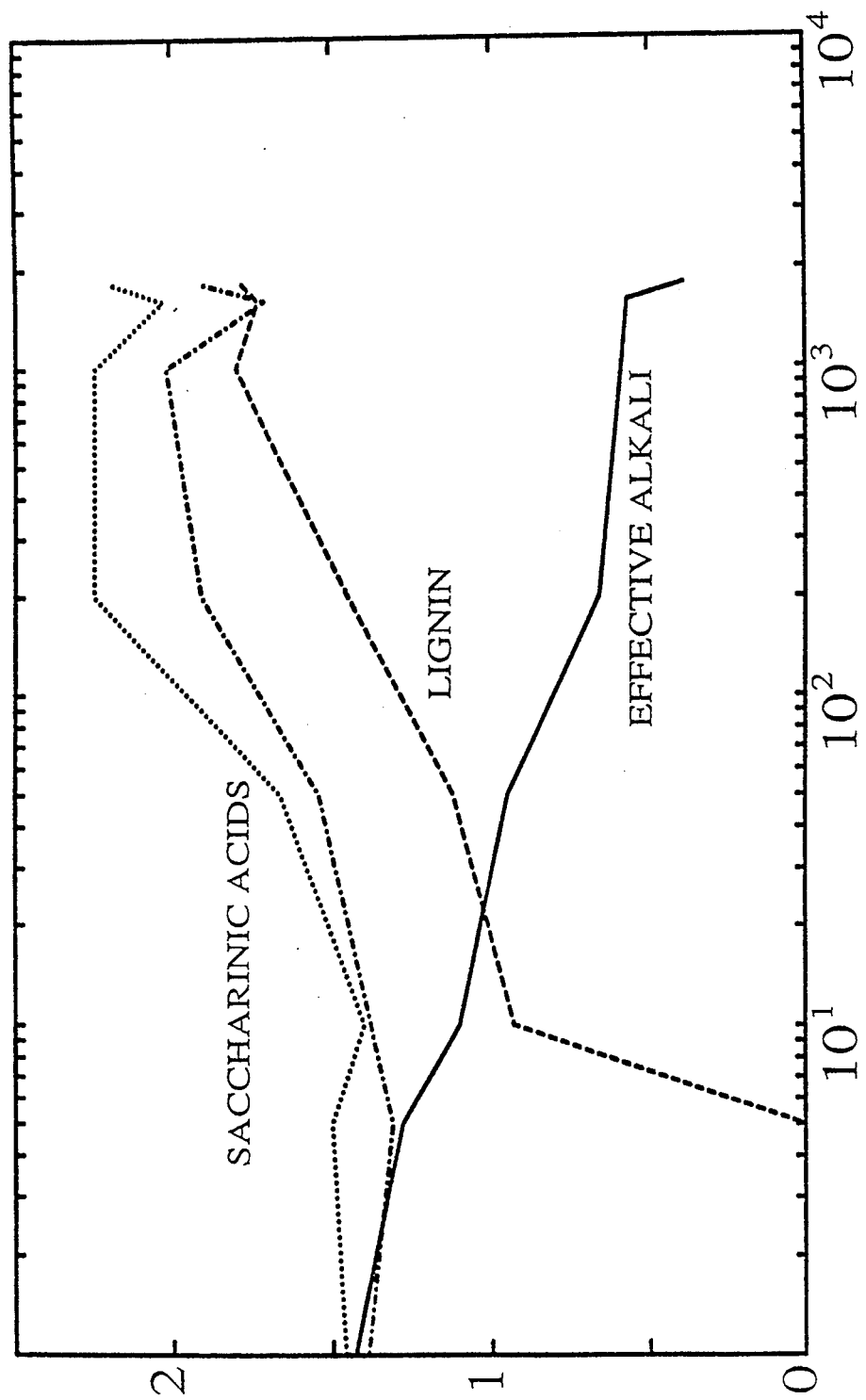
FIG. 9 is a graph of the evolution of the lignin, saccharinic acid, hemicellulose and effective alkali absorbances versus the H-factor obtained during cooking of softwood chips.

The evolution of the effective alkali during a laboratory kraft cook is shown in FIG. 8. The experimental conditions were: alkali charge, 16% (on o.d. wood) for softwood and 13% for hardwood; sulfidity, 25%; liquor-to-wood ratio, 4.5/1.0; time to cooking temperature, 80 minutes; cooking temperature, 170° C.; final H-factor, 1800 (softwood: jack pine) and 1100 (hardwood:aspen). Hardwood cooks are usually performed at a lower alkali charge than softwoods because of the lower lignin content in hardwood. Agreement between titration and infrared measurements is apparent. The effective alkali signal can thus be monitored throughout the cook. The sharp drop is EA for the softwood cook is seen at high H-factors, and probably indicates a marked loss in pulp yield. This is shown in FIG. 9 where the relative evolution of the lignin, saccharinic acid and effective alkali absorbances is displayed versus the H-factor obtained during cooking of softwood (jack pine) chips. The increase in the lignin peak at a wave number of 1491 cm$^{-1}$ tapers off near the end of the cook, indicating that bulk delignification is no longer taking place. On the other hand, after an initial increase, a decrease in both saccharinic acid peaks near the middle of the cook indicates that there is some decarboxylation of hemicellulose degradation products. This is followed by a sudden increase at the end of the cook which probably suggests that saccharinic acids originating from cellulose are now accumulating in the liquor.

EXAMPLE 5

Figure 10:
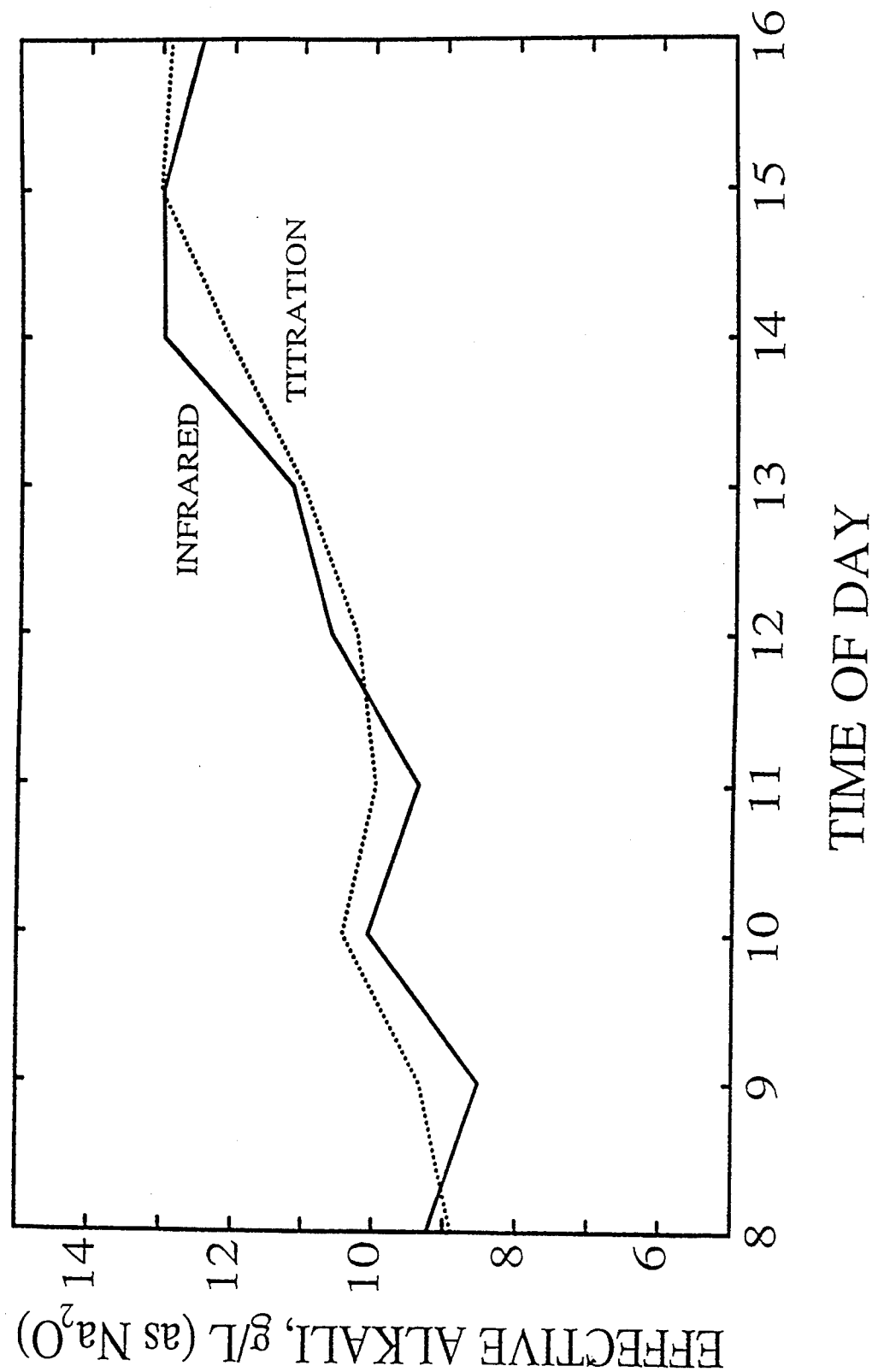
FIG. 10 is a graph of the value of residual effective alkali concentration of black liquor samples taken at hourly intervals from a typical mill continuous digester.

The change in residual effective alkali (REA) at hourly intervals in a typical full-scale mill digester is shown in FIG. 10. The coefficient of variation for this type of measurement is 4.5%. Comparison with titrimetric methods are very favourable.

From the above examples it can be seen that different liquors in the kraft pulping process can be analyzed and the effective alkali of liquors can be controlled by correlating the relationship between peak-absorbance measurements of samples with the peak absorbance for different alkali concentrations and thus determine an optimum effective alkali in the sample. Consequently the process can be controlled to obtain the optimum effect alkali of the liquor by varying at least one process variable.

Various changes may be made to the embodiments shown herein without departing from the scope of the present invention which is limited only by the following claims.

The embodiments of the present invention in which an exclusive property or privilege is claimed are defined as follows:

1. A method for controlling the operation of a recovery boiler in the preparation of kraft pulp wherein smelt is produced in a recovery furnace and fed to a smelt dissolving tank to form green liquor, which comprises the steps of:

withdrawing samples of a green liquor after the smelt dissolving tank;

subjecting the samples to infrared spectrophotometry at a wave number of about 1100 cm$^{-1}$ for sulfate and at a wave number of about 1000 cm$^{-1}$ for thiosulfate to produce peak-absorbance measurements relative to a background spectrum of water;

subjecting samples of sulfate and thiosulfate solutions of different known concentrations to infrared spectrophotometry at the same wave numbers in order to establish sulfate and thiosulfate calibration curves;

correlating relationships between the peak-absorbance measurements of the samples with the peak absorbances of the samples of sulfate and thiosulfate solutions to determine optimum sulfate and thiosulfate concentrations in the samples; and adjusting the recovery boiler operation as required to bring the sulfate and thiosulfate concentrations in the green liquor from the concentration thereof in the withdrawn samples, as determined by the peak-absorbance measurement thereof, to optimum concentration.

2. The method for controlling the operation of a recovery boiler according to claim 1 wherein the samples of green liquor are subjected to infrared spectrophotometry at a wave number of about 1030 cm$^{-1}$ to produce baseline-absorbance measurements and wherein baseline-absorbance measurements for different sulfate and thiosulfate concentrations are determined.

3. The method according to claim 1 wherein the spectrophotometry is performed in attenuated total reflectance.

4. The method according to claim 3 wherein a circular section attenuated total reflectance cell is used.

5. The method according to claim 3 in which a square section attenuated total reflectance cell is used.

6. The method according to claim 1 wherein the spectrophotometry is performed in a flow through cell for continuous measurements.

7. The method according to claim 1 wherein the relationships between the peak-absorbance measurements of samples with the peak absorbance for different alkali concentrations is obtained using least squares curve fitting.

* * * * *